(12) United States Patent
Looney

(10) Patent No.: US 11,319,225 B2
(45) Date of Patent: May 3, 2022

(54) MODULAR SYSTEM AND METHOD FOR MERCURY SPECIATION IN A FLUID SAMPLE

(71) Applicant: SAVANNAH RIVER NUCLEAR SOLUTIONS, LLC, Aiken, SC (US)

(72) Inventor: Brian B. Looney, Aiken, SC (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 641 days.

(21) Appl. No.: 16/169,036

(22) Filed: Oct. 24, 2018

(65) Prior Publication Data
US 2020/0131061 A1    Apr. 30, 2020

(51) Int. Cl.
| | | |
|---|---|---|
| *C02F 1/52* | (2006.01) | |
| *B01D 21/01* | (2006.01) | |
| *B01J 20/02* | (2006.01) | |
| *B01J 20/22* | (2006.01) | |
| *G01N 33/18* | (2006.01) | |
| *C02F 101/20* | (2006.01) | |
| *C02F 103/06* | (2006.01) | |

(52) U.S. Cl.
CPC ............ *C02F 1/5263* (2013.01); *B01D 21/01* (2013.01); *B01J 20/0233* (2013.01); *B01J 20/22* (2013.01); *G01N 33/1813* (2013.01); *B01D 2257/602* (2013.01); *B01J 2220/4806* (2013.01); *C02F 2101/20* (2013.01); *C02F 2103/06* (2013.01); *C02F 2201/007* (2013.01)

(58) Field of Classification Search
None
See application file for complete search history.

(56) References Cited

U.S. PATENT DOCUMENTS

| | | | |
|---|---|---|---|
| 3,693,323 A | 9/1972 | Gant | |
| 3,714,562 A | 1/1973 | McNerney | |
| 3,771,960 A | 11/1973 | Kim et al. | |
| 3,924,219 A | 12/1975 | Braun | |

(Continued)

FOREIGN PATENT DOCUMENTS

| | | |
|---|---|---|
| CN | 101629881 | 1/2010 |
| CN | 202057518 | 11/2011 |

(Continued)

OTHER PUBLICATIONS

Amde, et al. "Methods and recent advances in speciation analysis of mercury chemical species in environmental samples: a review" *Chemical Speciation & Bioavailability* 28(1-4) (2016) pp. 51-65.

(Continued)

*Primary Examiner* — Clare M Perrin
(74) *Attorney, Agent, or Firm* — Dority & Manning, P.A.

(57) ABSTRACT

Modular Hg analysis devices and methods are described for use in mercury speciation protocols. Modules can be selected and removably connected to one another to specifically target mercury species in a sample so as to accurately determine the presence or quantity of different mercury species in a fluid sample. Modules can include reductants for reducing inorganic mercury to form elemental mercury and amalgamation agents to capture the elemental mercury. Modules can include filters for capture of particulates as well as capture agents, e.g., solid phase extraction agents, for capture of organic mercury species.

16 Claims, 2 Drawing Sheets

(56) References Cited

U.S. PATENT DOCUMENTS

| | | | |
|---|---|---|---|
| 4,423,407 | A | 12/1983 | Zuckerman |
| 5,229,321 | A | 7/1993 | Takami |
| 5,480,549 | A | 1/1996 | Looney et al. |
| 5,492,627 | A | 2/1996 | Hagen et al. |
| 5,558,771 | A | 9/1996 | Hagen et al. |
| 5,753,109 | A | 5/1998 | Looney et al. |
| 6,129,843 | A | 10/2000 | Petty et al. |
| 6,280,625 | B1 | 8/2001 | Jackson et al. |
| 6,367,563 | B1 | 4/2002 | Looney et al. |
| 6,823,749 | B1 | 11/2004 | Welsh et al. |
| 7,059,206 | B1 | 6/2006 | Kingston et al. |
| 7,160,471 | B2 | 1/2007 | Looney et al. |
| 7,222,546 | B2 | 5/2007 | St. Germain |
| 7,276,161 | B2 * | 10/2007 | Rajan ............ C02F 1/003 210/266 |
| 7,285,419 | B2 | 10/2007 | Shade et al. |
| 8,011,239 | B1 | 9/2011 | Chadwick et al. |
| 8,034,246 | B2 | 10/2011 | Gustafsson et al. |
| 8,287,726 | B2 | 10/2012 | Williams et al. |
| 8,770,891 | B2 | 7/2014 | Looney et al. |
| 8,828,731 | B2 | 9/2014 | Alper |
| 8,911,630 | B2 | 12/2014 | Looney et al. |
| 9,199,192 | B2 | 12/2015 | Cooper |
| 9,399,912 | B2 | 7/2016 | McAlary et al. |
| 2005/0199047 | A1 | 9/2005 | Adams et al. |
| 2006/0257286 | A1 | 11/2006 | Adams |
| 2007/0122870 | A1 | 5/2007 | Turley et al. |
| 2008/0081376 | A1 * | 4/2008 | Hernandez ......... B01D 15/10 436/81 |
| 2009/0032472 | A1 | 2/2009 | Krogue et al. |
| 2009/0045149 | A1 | 2/2009 | Murray et al. |
| 2011/0068046 | A1 | 3/2011 | Tullos et al. |
| 2011/0070597 | A1 | 3/2011 | Vlahos et al. |
| 2013/0199996 | A1 | 8/2013 | Looney et al. |
| 2014/0371105 | A1 * | 12/2014 | Thomas ............ G01N 33/2835 506/15 |
| 2017/0023536 | A1 | 1/2017 | Brann |

FOREIGN PATENT DOCUMENTS

| | | |
|---|---|---|
| CN | 103743655 | 4/2014 |
| CN | 204188444 | 4/2015 |
| CN | 204188445 | 4/2015 |
| CN | 105080519 | 11/2015 |
| CN | 105148847 | 12/2015 |
| CN | 205679503 | 11/2016 |
| CN | 206074593 | 5/2017 |
| DE | 825909 C | 1/1951 |
| KR | 101682421 | 12/2016 |
| WO | WO 2003/076092 | 9/2003 |
| WO | WO 2003/095117 | 11/2003 |
| WO | WO 2008/045599 | 4/2008 |
| WO | WO 2009/017479 | 2/2009 |
| WO | WO 2010/014852 | 2/2010 |
| WO | WO 2016/128686 | 8/2016 |

OTHER PUBLICATIONS

Bireta, P. "Application of Diffusive Gradient in Thin-Film Passive Samplers to Assess Mercury Availability and Mobility in a Fresh Water River System" *The University of Texas at Austin* (2015).

Clarisse, et al. "Biomonitoring and assessment of monomethylmercury exposure in aqueous systems using the DGT technique" *Science of the Total Environment* 416 (2012) pp. 449-454.

Clarisse, et al. "Measurements of Dissolved Methylmercury in Natural Waters Using Diffusion Gradients in Thin Film (DGT)" *Journal of Environmental Monitoring* 8(12) (2006) pp. 1242-1247. (Abstract only).

Docekalova, et al. "Application of Diffusion Gradient in Thin Film (DGT) to Measurement of Mercury in Aquatic Systems" *Talanta* 65(5) (2005) pp. 1174-1178. (Abstract only).

Fernandez-Gomez, et al. "Diffusive gradients in thin films for predicting methylmercury bioavailability in fresh waters after photodegradation" *Chemosphere* 131 (2015) pp. 184-191.

Fernandez-Gomez, et al. "Comparison of different types of diffusive gradient in thin film samplers for measurement of dissolved methylmercury in freshwaters" *Talanta* 129 (2014) pp. 486-490.

Fernandez-Gomez, et al. "Development of the DGT Technique for Hg Measurements in Water: Comparison of Three Different Types of Samples in Laboratory Assays" *Chemosphere* 85 (2011) pp. 1452-1457.

Gao, et al. "A novel method for the determination of dissolved methylmercury concentrations using diffusive gradients in thin films technique" *Talanta* 120 (2014) pp. 470-474.

Huttenloch, et al. Use of Copper Shavings to Remove Mercury from Contaminated Groundwater or Wastewater by Amalgamation. *Environ. Sci. Technol.* 37 (2003) pp. 4269-4273.

Kallithrakas-Kontos, et al. "Recent Advances in the Analysis of Mercury in Water—Review" *Current Analytical Chemistry* 12 (2016) pp. 22-36.

Manning, G. "Non-Charcoal Diffusive Samplers" (2007) pp. 1-43.

Michaud, et al. "A Short-Term Diffusive Sampler for Nitrogen Dioxide Monitoring in Epidemiology" *J. Air & Waste Manage. Assoc.* 41(11) (1991) pp. 1483-1488.

Paller, et al. "Development of methods for measuring bioavailable metals & mercury species using Diffusive Gradients in Thin film (DGT) technology" (2017).

Paller, et al. "Long Term Changes in Mercury Concentration in Fish from the Middle Savannah River" *Science of the Total Environment* 382(2-3) (2007) pp. 375-382. (Abstract only).

Panichev, et al. "Influence of Different Cooking Procedure on the Hg Concentration in Fish" *Journal of Fisheries Sciences* 10(1) (2016) pp. 63-69. (Abstract only).

Pei, et al. "Individually Addressable Gel-Integrated Voltammetric Microelectrode Array for High-Resolution Measurement of Concentration Profiles at Interfaces" *Anal. Chem.* 73 (2001) pp. 2273-2281.

Peinjenburg, et al. "Passive Sampling Methods for Contaminated Sediments: State of the Science for Metals" *Int. Env. Assessment & Management* 10(2) (2014) pp. 179-196.

Pelcova, et al. "Development of the Diffusive Gradient in Thin Film Technique for the Measurement of Labile Mercury Species in Waters" *Analytica Chimica Acta* 819 (2014) pp. 42-48. (Abstract only).

Rekhi, et al. "A Review on Recent Applications of High-Performance Liquid Chromatography in Metal Determination and Speciation Analysis" *Crit Rev Anal Chem.* 47(6) (2017) pp. 524-537. (Abstract only).

Skogvold, S. "Development and properties of nontoxic solid electrodes for environmental Surveillance" *Norwegian University of Science and Technology* (2009).

Related U.S. Applications, Oct. 24, 2018.

* cited by examiner

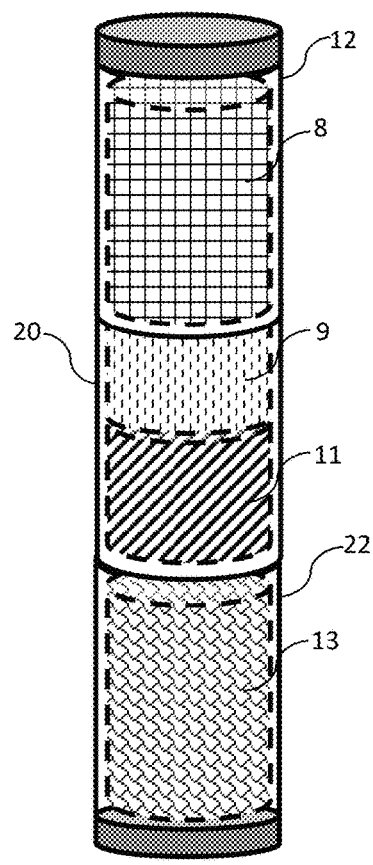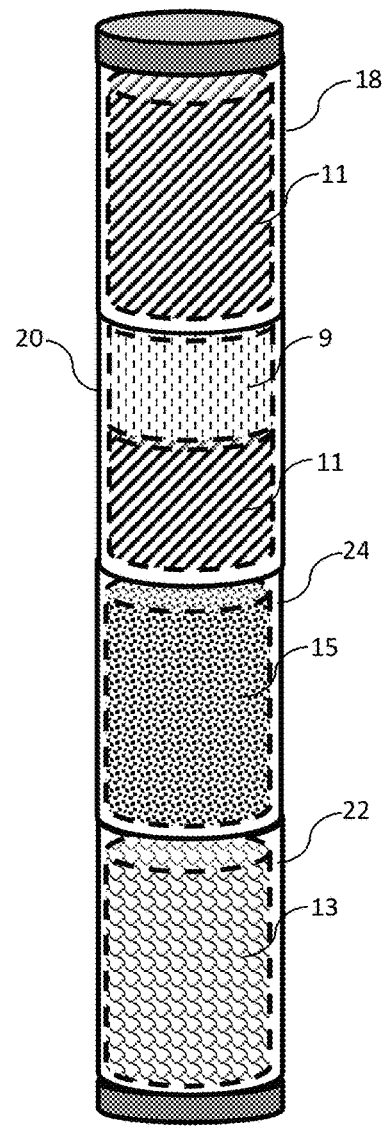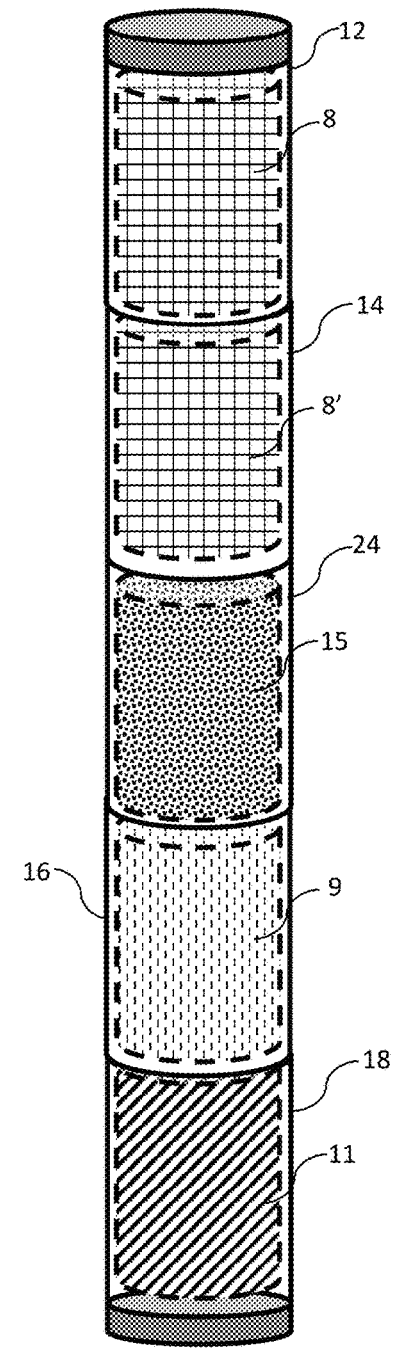
FIG. 3
FIG. 4
FIG. 5

MODULAR SYSTEM AND METHOD FOR MERCURY SPECIATION IN A FLUID SAMPLE

FEDERAL RESEARCH STATEMENT

This invention was made with government support under Contract No. DE-AC09-08SR22470 awarded by the U.S. Department of Energy. The government has certain rights in the invention.

BACKGROUND

Mercury (Hg) is an important and persistent environmental pollutant that is bioaccumulative and toxic in even small amounts. There are many stable Hg species, with different species exhibiting different characteristics including toxicity, solubility, mobility and bioavailability. Organic Hg and in particular methylmercury ($[CH_3Hg]^+$; MeHg) is one of the most toxic Hg species affecting human and animal health. Hg can be found naturally in the environment, as well as a result of anthropogenic activities such as mining, Hg manufacture and disposal, and fossil fuel combustion.

Hg contamination has become a global concern as it is often released into the atmosphere in one location with impact on ecosystems in another location, which can be thousands of kilometers away. When Hg enters in an aqueous system, it is subject to methylation, forming MeHg, and demethylation, forming inorganic Hg (InHg), primarily ionic $Hg^{2+}$ and labile complexes such as $HgCl_2^0$. Once in the biosystem, MeHg partitions into periphyton, plankton and biota that are eaten by invertebrates and fish. As a result, MeHg bio-magnifies as it accumulates throughout and up the food chain.

Due to both the toxicity as well as the bio-magnification in the food chain, monitoring both total Hg and Hg species is of high importance to assess potential impacts on human and animal health as well as the environment; additionally, understanding spatial and seasonal variability and lability of Hg species in the environment is important to refine the technically based assessment of risks.

What are needed in the art are methods and devices that can provide simple and affordable protocols for Hg monitoring and risk assessment. More specifically, what is needed is a device that can effectively provide information with regard to the presence and/or quantity of particular Hg species in an environment so as to better assess risk. Moreover, methods and devices that differentiate organic Hg from inorganic and elemental Hg and which can be modified and individualized so as to simply and accurately determine the presence and/or concentration of specific Hg species in an aqeuous sample would be of great benefit.

SUMMARY

According to one embodiment, disclosed is a modular Hg speciation device that includes a plurality of modules that can be mixed and matched depending upon the particular protocol and mercury species of interest. For instance, a device can include a filtration module that can physically filter a sample to remove particles of a predetermined size from a fluid sample. Optionally, a device can include multiple filtration modules that exhibit varying porosity and/or varying attraction so as to retain particulates of different sizes or different composition in the different filtration modules. In addition, a device can include a reduction module that includes a reductant configured to interact with and reduce inorganic and ionic Hg species to form elemental Hg. A device can also include an amalgamation agent that is configured to form an amalgam with elemental mercury. The amalgamation agent can be retained in a module and utilized to capture elemental Hg flowing through the module. In one embodiment, a single module can include both a reductant and an amalgamation agent. Optionally, a device can include a module that includes a reductant and a separate module that includes an amalgamation agent, such that these two functions can be carried out in two separate modules. A device can also include a capture module that is configured to retain one or more Hg species, e.g. total mercury of any species in one embodiment.

Also disclosed is a method for examining a fluid sample to determine the presence or quantity of one or more mercury species in the sample. A method can include sequentially contacting a plurality of modules with a fluid sample. As the fluid sample contacts each consecutive module, components of the fluid sample can be removed from the sample (e.g., via filtration, extraction, amalgamation, etc.) or altered (e.g., reduced, functionalized) through the contact. A method can also include analyzing the modules or effluent from one or more of the modules and thereby determining the presence or quantity of an Hg species in the fluid sample. For instance through analysis of an amalgamation module, the presence or quantity of retained elemental Hg can be directly or indirectly determined, and this data can provide information concerning the presence or quantity of inorganic Hg in the starting fluid sample. Similarly, through the analysis of a module that is designed to retain organic Hg species, the presence or quantity of the organic Hg species in the aqueous sample can be determined.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 3 illustrates another combination of modules as may be utilized in an analysis protocol.

FIG. 4 illustrates another combination of modules as may be utilized in an analysis protocol.

FIG. 5 illustrates another combination of modules as may be utilized in an analysis protocol.

Figure 1:
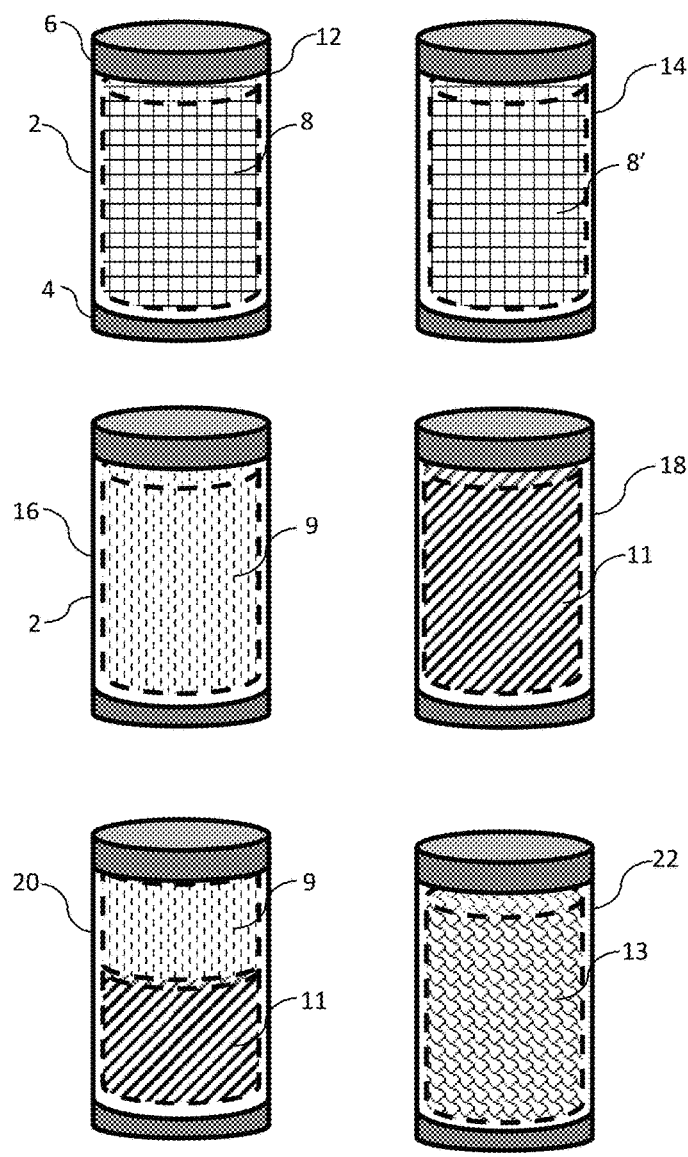
FIG. 1 schematically illustrates several different modules as may be included with a device.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to modular Hg analysis devices and methods that can be utilized in Hg speciation protocols. More specifically, disclosed devices can be utilized to modify targeted Hg species and/or separate Hg species from one another by use of separable modules, so as to accurately determine the presence or quantity of different Hg species in a fluid sample.

The devices include multiple different modules, and the different modules can be mixed and combined in any desired fashion and in any order so as to target Hg species of interest in an analysis protocol. In one embodiment, the modules can be removably attachable to one another such that multiple different modules can be connected to provide a single unitary device. A unitary device can be used to sequentially contact a single sample with each consecutive module as the sample flows (or is caused to flow) through the unitary device. Alternatively, modules can be used individually and separated from one another, and a sample can be sequentially contacted with each module of interest, but not necessarily immediately contacted via flow out of one module and directly into another. For instance, in one embodiment, a sample can flow through a first module. Within that module, species of the sample can be modified or retained in the module, and the effluent from that first module can be collected. That collected effluent can then be subjected to one or more activities, e.g., stored, modified, transported, analyzed, heated, cooled, etc., prior to contact with a second module, and so on. Thus, the modular analysis of a sample can be carried out in a single unitary device that includes multiple combined modules, in separated modules, or some combination thereof, as desired. In all embodiments the sample is passed through the device or contacted with selected modules individually, generally followed by contact with a rinse solution to assure that only the desired mercury species remain for subsequent quantification. Contact with individual modules can be carried out in any fashion. For instance, a device can be poured through a module that is pre-loaded with an active agent (e.g., a reductant, and amalgamation agent, etc.), or alternatively, the active species of a module can be added to the module (i.e., the housing) in conjunction with addition of the sample to attain the desired contact.

In one embodiment, a device can be utilized to examine an aqueous liquid sample, but this is not a requirement of the devices and methods, and the modular devices can be utilized to examine any fluid sample for one or more Hg species. As utilized herein, the term "fluid sample" generally refers to any sample that is composed primarily (but not exclusively) of gaseous and/or liquid fluid(s) and can encompass a gaseous sample such as air, a vaporous sample such as steam, or a liquid sample such as an aqueous liquid sample as may be obtained from any source (e.g., ground water including stream, lake, or well water, pore water, etc.).

FIG. 1 schematically illustrates several different modules 12, 14, 16, 18, 20, 22 as may be included with a device. In general, each module can include an external housing 2, end-connectors 4, 6, and a substrate 8, 8', 9, 11, 13 incorporated within and retained by the housing 2. The housing can be, e.g., a glass, metal, quartz, ceramic, or polymeric housing formed to the desired size and shape according to standard practice. In one embodiment, the housing can be designed to withstand high temperatures (e.g., about 750° C. or higher in some embodiments. Such embodiments can be useful for those applications in which the sample is analyzed while retained on/in the housing and the analysis can include a high temperature analysis protocol, e.g., use of a direct mercury analyzer.

The size of individual modules as defined by the housing and end-connectors is not particularly limited. In one embodiment, the modules can be quite small, e.g., microcolumns, which can be useful in examining relatively small sample sizes. For instance, individual modules can have an inner cross-sectional dimension of from about 5 mm to about 25 mm, with a total housing volume of about 200 mL or less. Microcolumn sizing is not a requirement of disclosed devices, however, and in other embodiments, individual modules can be larger, e.g., on the order of several inches in length or cross-sectional dimension.

A substrate retained within the housing of a module can carry or directly provide the desired functionality to a module and can vary between the different modules. In general, a substrate can have a high surface area, e.g., in a range of about 20 $m^2/g$ to about 800 $m^2/g$ and can be of any suitable material(s) and construction so as to allow flow therethrough and contact between functional components of a module and a fluid sample that passes through the module.

Exemplary materials for use in forming a substrate can include, without limitation, organic or inorganic polymers, glass, quarts, ceramic or any combination thereof. Organic polymers as may be utilized in forming a substrate can include, without limitation, cellulose, polyamides (e.g., nylons), polyolefins, polyesters, polyurethanes, polyvinylhalides, or a combination thereof. In one embodiment, a substrate can include polytetraflouroethylene (PTFE) as a material of formation.

A substrate can generally be of a fibrous, particulate, hydrogel, or porous membrane construction, as well as combinations thereof. A fibrous web (e.g., a woven or nonwoven fibrous web) for use in forming a substrate can include fibers of any suitable diameter. For instance, a nonwoven fibrous web can include a plurality of microfibers, for instance of thermoplastic, melt-blown polymeric materials. As utilized herein, the term microfiber generally refers to fibers having an average fiber diameter of about 50 μm or less, for instance from about 2 μm to about 25 μm in some embodiments. A fibrous web is not limited to incorporation of microfibers, however, and a substrate can incorporate large-diameter fibers, for instance large diameter melt-extruded fibers that have been mechanically-calendared, air-laid, or spunbonded. As utilized herein, the term "large-diameter fiber" generally refers to fibers having an average fiber diameter of about 50 μm to about 500 μm. By way of example, a nonwoven web made from large-diameter staple fibers as can be formed on carding or air-laid machines as is well known in the art can be utilized in forming a substrate. For instance, a fibrous web can be rolled, layered, or otherwise formed so as to function as a substrate that partially or totally fills a housing of a module.

The substrate of a module can have a unitary construction, e.g., a self-supporting foam or fibrous construction or can include a plurality of individual components (e.g., particles) held together only by the housing of the module. In one embodiment, a substrate can include a binder that is applied to components that form the substrate (e.g., the fibers). Curing of this binder can adhesively attach the substrate components to one another and optionally also to the module housing.

Referring again to FIG. 1, included among the modules of a device can be a filter module 12. Filter modules can be utilized to separate particulates from a sample. A filter module 12 can physically block flow-through of all particulates larger than the mesh size of the substrate 8 and can be formed of materials as described above, e.g., fibers, particulates, porous membranes, or combinations thereof. For instance, a filter module 12 can include pores in a range of about 0.3 μm to about 5 μm, can be fibrous or non-fibrous in nature, with exemplary formation materials including, but not limited to polymers, glass, quartz, ceramic, or any combination thereof.

A filter module 12 can be particularly beneficial when utilizing a device in a field application, for instance for removal in the field of sediment from an environmental liquid sample taken from a natural water source.

A device can include multiple filter modules. For instance, a device can include a first filter module 12 having a mesh size designed to remove larger sediment from a liquid sample source, and can include a second filter module 14 that can have a smaller mesh size, for instance, a mesh size designed to capture particulates as may be entrained in a vapor a gaseous fluid sample. Thus, a filter module of a useful mesh size can be selected for use in a protocol depending upon the particular characteristics of the sample materials to be analyzed. However, in other protocols, in which the sample is pre-filtered or known to not include particulates, the system can be used without inclusion of the filter module 12 (for instance in laboratory techniques).

Of course, multiple filter modules can also be used together in a protocol. For instance, when a sample is suspected of including different types of particulates that are of different sizes, a system can utilize both a first filter module 12 including a substrate 8 that can capture larger particulates and a second filter module 14 including a smaller mesh substrate 8' that can capture smaller particulates. Such a design may be particularly beneficial in protocols in which particles in a known size range are expected to contain Hg, while larger (or smaller) particles are expected to be Hg-free. Thus, Hg-containing particles can be concentrated and separated from other particles of the sample, and all particles over a designated mesh size can be removed from the fluid sample.

To provide for speciation of Hg in a protocol, one or more modules of a device can incorporate aspects of reactive chemistry so as to selectively separate Hg species as they sequentially contact modules of the device. Separation can be carried out by selective reaction and capture of targeted Hg species. More specifically, at least one reductant module 16 of a device can include a reductant 9 that can react with and reduce a targeted Hg species (e.g., ionic and/or inorganic Hg species) of a fluid sample to form elemental Hg, and the reductant 9 will not interfere with or modify other non-targeted Hg species (e.g., organic Hg species) that may be present in the fluid sample.

The reductant 9 can be any material that can react with inorganic Hg species of a fluid sample including labile Hg complexes (e.g., $HgCl_2^0$) and ionic Hg species (e.g., $Hg^{2+}$ and/or $Hg^{1+}$) to form elemental Hg. Hg reductants as are known in the art can be utilized including, without limitation, stannous salts (e.g., stannous chloride, Sn(II)Cl), elemental copper, elemental zinc, etc., as well as combinations of one or more Hg reductants.

The reductant 9 can simply be applied to the surface of a supporting substrate or can be a component of the as-formed substrate of the module 16. For example an amount a reductant of choice (e.g., a stannous salt, copper-containing particulates, etc.) can be applied to the surface of a fibrous web that can then be loaded into the housing of a module 16 and form the active substrate that includes the reductant 9 of the module 16.

The supporting substrate for the reductant 9 of the module 16 can generally include a porous matrix within which the reductant can be loaded or impregnated. For example, a high surface area particulate substrate such as silica, alumina, zirconia, etc. can be coated with a reductant 9 and the active particulates can be loaded into a housing 2 to form a reductant module 16.

By way of example, a high surface area, uncoated, supporting substrate (such as silica) can be first loaded into the housing 2 of a module 16, and the supporting substrate can subsequently be treated with a solution so as to apply the reductant, or a precursor thereof (e.g., a stannous salt solution) to the supporting substrate. The solution can coat the surface of the supporting substrate as well as any pores of the supporting substrate. Following, the coating can be treated as necessary to provide the reductant 9 within the module 16.

In addition to a reductant 9 for reducing inorganic/ionic Hg to form elemental Hg, a device can include an amalgamation agent 11 to amalgamate and capture the elemental Hg. The reductant 9 and the amalgamation agent 11 can be located in the same or different modules. In one embodiment, a device can include multiple modules so as to provide both options to a user. For instance, a device can include a module 16 that incorporates a reductant 9, a module 18 that includes an amalgamation agent 11, and a module 20 that includes both reductant 9 and amalgamation agent 11, which can be either separated from one another within the module 20 as shown in FIG. 1, or alternatively combined together throughout all or a portion of a single module. In those embodiments in which inorganic Hg is to be reduced and captured, an amalgamation agent 11 will by necessity be located either downstream in the same or a separate module or combined together with a reductant in a single module of a device. However, in those embodiments in which a sample is examined for in situ elemental Hg, it may be preferred to locate a module 18 including an amalgamation agent upstream of any reducing agents that could modify an inorganic Hg component of a sample to form elemental mercury.

The amalgamation agent 11 can selectively retain elemental Hg while allowing other Hg species to pass by and continue to flow out of the module 18. Almost all metals can form an amalgam with elemental Hg, with notable exceptions including iron, platinum, tungsten, and tantalum. However, some metals are more efficient at amalgam formation than others. Accordingly, in some embodiments, it may be beneficial to incorporate such a metal as an amalgamation agent 11. By way of example, in one embodiment an amalgamation agent 11 can include elemental gold, silver, copper, zinc, tin, or combinations thereof, optionally in conjunction with one or more additional amalgam-forming materials, so as to selectively retain elemental Hg of an as-gathered sample or to retain elemental Hg formed via reaction of the reductant 9 with inorganic Hg of a fluid sample.

In one embodiment, the device can include a module in which the amalgamation agent is the same material as the reductant. For instance, copper and zinc can both function as a reductant for ionic and inorganic Hg species as well as forming an amalgam with the resulting elemental mercury. Accordingly, in one embodiment, a module can incorporate copper and/or zinc that can provide for both reduction and amalgamation of the reduction product elemental Hg.

The amalgamation agent 11 can be applied to the surface of a supporting substrate similar to methods used for a reductant 9, as described above. For instance, in one non-limiting example, a particulate substrate can be coated with a solution that provides the amalgamation agent 11 or a precursor thereof. In one embodiment, a solution of a metal salt (e.g., a methanol based solution including a combination HCl/methanol/hexane solvent and a gold chloride in an amount up to saturation of the solution) can be applied to a particulate substrate (by e.g., simply soaking the particulate in the solution). Following, the solvent can be removed (by e.g., air drying or applied heat) and the metal salt reduced to provide an elemental metal amalgamation agent 11 that is carried by a particulate substrate.

Another module that can be included with a device is a capture module 22 that can include a solid phase extraction agent or the like for retaining one or more Hg species (e.g., one or more targeted organic Hg species or total Hg). In one embodiment, a capture module 22 can incorporate an active hydrogel 13, with the hydrogel 13 of the capture module 22 including a suitable capture agent for the Hg species of interest. A capture module 22 can retain the targeted Hg species by any useful retention chemistry including, without limitation, covalent or noncovalent bond formation, e.g., charge/charge interaction, adsorption, absorption, etc. For example, Hg retention in a capture module 22 can be obtained by incorporation of an ion-exchange resin as the active hydrogel 13 in the capture module 22.

In the embodiment of FIG. 1, the system includes a single capture module 22, which can generally be a total Hg capture module, but a device can optionally include different or additional capture modules (e.g., additional capture layers designed to capture specific Hg compounds).

In one embodiment a capture module 22 can incorporate binding capability that can retain all Hg species that are not selectively captured by another module (e.g., Hg-containing particulates captured in a filter module 12 and elemental Hg captured in an amalgamation module 18). As such, binding agent(s) of a capture module 22 need not selectively bind Hg species, but can incorporate generic Hg complexing agents capable of retaining multiple Hg species thereon. For instance, the capture module 22 can include one or more agents capable of forming a complex with multiple Hg-containing species. Such agents can include, without limitation, organic thiols and/or dithiocarbamates in combination with $Au^{+3}$ or other complexing agents such as acidic mixtures containing dithiol species. For instance, a capture module 22 can incorporate an ion exchange resin hydrogel 13 capable of retaining multiple Hg species thereon. In one embodiment, a capture module 22 can incorporate a thiol-functionalized resin hydrogel 13, e.g., a thiol-functionalized resin incorporated into a polyacrylamide or other suitable hydrogel. In one particular embodiment, a capture module 22 can incorporate a 3 mercapto-propyl functionalized silica gel immobilized in a polyacrylamide gel.

As mentioned previously, each module can include end connectors 2, 4. Connectors can be employed in order to connect modules to one another and optionally to fluid tubing lines for in-flow or out-flow to/from a device. Each connector may comprise a simple conventional tubing connection fitting or end fitting including a coupling nut, a tubular coupling body and a ferrule that can connect to either a fluid tubing or to another module of the system. In one embodiment, the connectors may comprise components designed so as to not require an installation tool.

During use, selected modules may be connected to or used in conjunction with one another so as to provide optimum separation for a particular type of analysis, a particular analysis protocol, or a particular type of sample. Optimal separation or concentration of any particular Hg species can include a predetermined combination of modules. The utilization of connectors can allow for different modules to be rapidly swapped out and replaced with different modules that are better suited to a subsequently run analysis or analysis protocol or to a replacement module of the same type. In addition, the end connectors 2, 4, and provide for attachment to tubing lines that can be fluid input or output lines and in one embodiment that can connect a module directly to an analysis device (liquid or gas chromatograph, mass spectometry, etc.)

Figure 2:
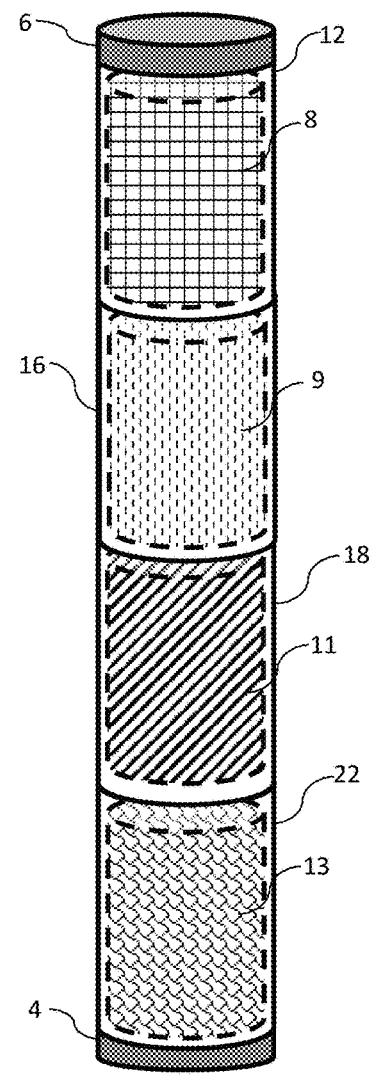
FIG. 2 illustrates one combination of modules as may be utilized in an analysis protocol.

The multiple different modules available for use in a protocol can be combined and connected in any order. For instance, FIG. 2 illustrates one exemplary embodiment in which a single unitary device is formed including a filter module 12, a reductant module 16, an amalgamation module 18, and a capture module 22. During use, a sample can be caused to flow through the device from the inlet connector 6 to the outlet connector 4. Flow through the device can be passive or active. For instance, gravity flow alone can be used or alternatively, flow can be encouraged via connection of a pump, e.g., a vacuum pump, to the outlet connector 4. In any case, sample flow into to the inlet end at inlet connector 6 of the device of FIG. 2 will first encounter the filter module 12 where sediments or other solids can be separated from the remainder of the sample. Downgradient to the filter module 12, the sample fluid can contact the reductant module 16, within which inorganic and ionic Hg species of the sample can react with the reductant 9 to form elemental Hg. Downgradient of the reductant module 16, the fluid (now carrying the elemental Hg reaction product) can contact the amalgamation module 18, within which the amalgamation agent 11 can selectively retain the elemental Hg. Thus, elemental Hg will pass no further through the device and into the capture module 22. However, the remainder of the sample fluid, and in particular any Hg species not selectively retained at the filter module 12 or the amalgamation module 18 can pass into the capture module 22. In one embodiment, as discussed previously, the capture module 22 can be configured to non-selectively capture all Hg species. As such, any remaining Hg species (i.e., those not selectively retained by the amalgamation agent 11 in module 18) can be captured in the capture module 22 by the hydrogel 13.

As mentioned previously, however, the particular order and selected modules of a device are not limited, and other modules and order thereof can be utilized in other embodiments. For instance, in the embodiment illustrated in FIG. 3, a module 20 is utilized in which the reductant 9 and the amalgamation agent 11 are co-located in the same module 20. In this embodiment, the reductant 9 and the amalgamation agent 11 are both located in a module 20, that is between a filter module 12 and a capture module 22. Thus, particulates larger than the mesh size of the filter module 12 can initially be captured in the filter module 12, inorganic and ionic Hg species can then react with the reductant 9 to form elemental Hg in the reductant/amalgamation module 20, and the elemental Hg can also be selectively retained by the amalgamation agent within the module 20. As the reductant 9 and the amalgamation agent 11 are both located in the module 20, both the reaction and the selective retention can take place in module 20 and elemental Hg species will not pass into the capture module 22. However, other Hg species that are not selectively retained by the amalgamation agent 11, can pass through the module 20 and be retained by the hydrogel 13 in the capture module 22.

FIG. 4 illustrates another embodiment of a device. In this embodiment, the first module of the device is an amalgamation module 18. Thus, in this embodiment, the first module of the device can capture elemental Hg in a sample. The second module of this particular embodiment is a reductant/amalgamation module 20 within which the module 20 can incorporate both the reductant 9 and the amalgamation agent 11. As such, elemental Hg of a sample can initially be captured in the module 18, and following, inorganic/ionic Hg species can be reduced and captured in the module 20, and a protocol can differentiate elemental Hg in a sample from inorganic/ionic Hg in a sample. Downstream of the module 20, this embodiment can include a capture module 24 that can incorporate a selective resin 15 for one or more particular Hg species, and this resin can differ from the resin 13 of the more generic capture module 22 that is downstream of the module 24. Thus, in this embodiment, elemental Hg of a sample can be captured at module 18, inorganic/ionic Hg of a sample can be captured at module 20, a specific Hg species (e.g., a particular organic Hg species) can be preferentially captured at module 24, and any remaining Hg species can be captured at module 22. Of course, in such an embodiment, the reductant 9 and amalgamation agent 11 can alternatively be provided in separate modules, as discussed previously.

FIG. 5 illustrates yet another embodiment of a device as disclosed. In this embodiment, the device need not include a module 22 including a resin 13 that non-selectively retains those Hg species not retained in other modules. Thus, in this embodiment, only the predetermined targeted species are retained. For example, larger particulates can be retained in a first filter module 12 according to the mesh size of the substrate 8 and following, smaller particulates can be retained in a second filter module 14 according to the smaller mesh size of the substrate 8'. A specifically targeted Hg species can be retained in the specific capture module 24. In addition, inorganic and ionic Hg species of the sample can be reduced at reduction module 16 and then captured via amalgamation at the amalgamation module 18. Any other Hg species of the original sample can pass through the device and be captured in the outflow or released, as desired.

Whatever the arrangement of the modules, a device can include amounts of the active agents (reductant, amalgamation agent, capture agents) so as to efficiently react with and retain the targeted species in each selected module without interfering in flow of the sample carrying any remaining Hg species through the device. For instance a module 20 that includes both the reductant 9 and the amalgamation agent 11 within the module 20 can generally include from about 0.05% to about 20% by weight of the active material(s) (i.e., the total amount of reductant and/or amalgamation agent) as compared to the weight of the substrate material of the module absent the active materials. This range can be larger or smaller, however for some embodiments.

Following completion of a sampling protocol, the modules can be examined for either direct or indirect determination of the presence or quantity of the Hg species retained therein. Indirect determination methods can include, for example and without limitation to, elution of Hg species off the module followed by examination of the eluent. Direct determination methods can include, for example and without limitation to, mass analysis of the module or all or a portion of the substrate retained within the module.

For example, in one embodiment, the substrate 8 can be removed from the housing 2 of a filter module 12 for total particulate analysis. The particulate analysis can include further analysis of the particulates for specific content or simply total particulate mass analysis, as desired.

Contents of other modules can be removed, either in conjunction with the carrier substrate or by elution of the targeted species off of the solid phase media, as desired. For example, Hg species of a single module can be removed by separation of the module from any connected modules, solvent extraction of the solid phase carried by the module (e.g., via hexane extraction), and analysis of the extracted materials, e.g., via chromatography, mass spectrometry, etc.

In a direct analysis method, a module can be opened and the substrate media can be removed to be analyzed. For example, a cross section of the module substrate can be removed, and this cross section can be processed with acid digestion followed by atomic absorption spectroscopy. The mass of the solid phase substrate (or a known portion thereof) can be recorded and an Hg concentration by mass of the substrate can be determined. Through knowledge of the complete mass of the substrate of the module and the flow rate and time of flow that the module was subjected to, analysis can determine concentration of mercury in the stream per volume.

Disclosed methods and devices can be utilized to provide improved information of Hg presence and activity in sample sources. For instance, as methyl Hg is selectively taken up by aquatic invertebrate species, devices that selectively retain methyl Hg in a module can serve as a surrogate for aquatic organisms.

Devices can be conveniently utilized in a wide variety of applications. In particular, devices can be utilized in both liquid (e.g., aqueous) applications as well as for Hg speciation of gaseous or vaporous samples. For example, devices can be utilized to sample water sources (e.g., fresh or salt water; lakes, rivers, ponds, swamps, etc.; underground (e.g., wells) or above ground, etc.) as well as air sources (e.g., industrial off-gases, high or mid-level atmospheric samples, etc.), just to name a few.

While certain embodiments of the disclosed subject matter have been described using specific terms, such description is for illustrative purposes only, and it is to be understood that changes and variations may be made without departing from the spirit or scope of the subject matter.

What is claimed is:

1. A modular mercury speciation device comprising:
    a first filter module, the first filter module containing a first substrate defining a first mesh size configured to capture particles larger than the first mesh size of the substrate;
    a first amalgamation module comprising a first amalgamation agent, the first amalgamation agent configured to form an amalgam with elemental mercury, wherein the first amalgamation module is configured for removable attachment to the first filter module such that upon attachment to one another, a fluid flowing through the device will flow into the first amalgamation module following flow through the first filter module;
    a reduction module, the reduction module comprising a reductant configured to interact with and reduce inorganic and ionic mercury species to form elemental mercury, wherein the reduction module is configured for removable attachment to the first amalgamation module such that upon attachment to one another, fluid flowing through the device will flow into the reduction module following flow through the first amalgamation module;
    a second amalgamation agent, the second amalgamation agent forming an amalgam with elemental mercury, wherein upon assembly of the device the second amalgamation agent is located in the reduction module or downstream of the reduction module in a second amalgamation module; and a first capture module, the first capture module comprising a capture agent configured to bind an organic mercury species; wherein
the first capture module is removably attachable to at least one of the other modules.

2. The device of claim 1, further comprising a second filter module, the second filter module comprising a second substrate defining a second mesh size that differs from the first mesh size.

3. The device of claim 1, the reduction module comprising the second amalgamation agent.

4. The device of claim 1, comprising the second amalgamation module comprising the second amalgamation agent.

5. The device of claim 1, wherein the reductant and the second amalgamation agent are the same material.

6. The device of claim 1, wherein the reductant comprises a tin, copper, or zinc.

7. The device of claim 1, wherein the first amalgamation agent and the second amalgamation agent each independently comprise gold, silver, copper, tin, or zinc.

8. The device of claim 1, wherein the capture agent is configured to bind a plurality of mercury species.

9. The device of claim 8, wherein the capture agent comprises an organic thiol or a dithiocarbamate in combination with gold.

10. The device of claim 1, further comprising a second capture module.

11. A method for examining a fluid sample comprising mercury, the method comprising:
connecting the first filter module, the first amalgamation module, the reduction module, optionally the second amalgamation module, and the first capture module of claim 1 to obtain the modular mercury speciation device of claim 1;
flowing the fluid sample comprising mercury through the device of claim 1 such that the fluid sample contacts the first filter module, the first amalgamation module, the reduction module, the second amalgamation agent, and the first capture module, thereby separating elemental mercury, inorganic and ionic mercury, and organic mercury of the sample from one another.

12. The method of claim 11, further comprising following the contact, examining the contents of each of the first filter module, the first amalgamation module, the reduction module, the second amalgamation module when present, and the first capture module.

13. The method of claim 12, the examination comprising eluting a captured content off of at least one of the first filter module, the first amalgamation module, the reduction module, the second amalgamation module when present, and the first capture module.

14. The method of claim 12, the examination comprising a mass analysis of at least one of the first filter module, the first amalgamation module, the reduction module, the second amalgamation module when present, and the first capture module.

15. The method of claim 11, wherein the fluid sample is an aqueous sample.

16. The method of claim 15, wherein the aqueous sample comprises ground water.

* * * * *